US012648982B2

(12) United States Patent
Chow

(10) Patent No.: US 12,648,982 B2
(45) Date of Patent: Jun. 9, 2026

(54) HERBAL MEDICINE COMPOSITION AND METHODS OF USING SAME

(71) Applicant: CMOL PHARMACEUTICALS AUSTRALIA PTY LTD, North Willoughby (AU)

(72) Inventor: Ping Kwan Chow, North Willoughby (AU)

(73) Assignee: CMOL PHARMACEUTICALS AUSTRALIA PTY LTD, North Willoughby (AU)

(*) Notice: Subject to any disclaimer, the term of this patent is extended or adjusted under 35 U.S.C. 154(b) by 0 days.

(21) Appl. No.: 19/201,139

(22) Filed: May 7, 2025

(65) Prior Publication Data

US 2025/0262266 A1     Aug. 21, 2025

Related U.S. Application Data

(63) Continuation of application No. PCT/AU2024/050004, filed on Jan. 8, 2024.

(30) Foreign Application Priority Data

Jan. 9, 2023    (AU) ................................. 2023900032

(51) Int. Cl.
A61K 36/884       (2006.01)
A61K 36/185       (2006.01)
A61K 36/284       (2006.01)
A61K 36/752       (2006.01)
A61P 1/08         (2006.01)

(52) U.S. Cl.
CPC .......... *A61K 36/884* (2013.01); *A61K 36/185* (2013.01); *A61K 36/284* (2013.01); *A61K 36/752* (2013.01); *A61P 1/08* (2018.01)

(58) Field of Classification Search
CPC .. A61K 36/884; A61K 36/185; A61K 36/284; A61K 36/752; A61P 1/08
See application file for complete search history.

(56) References Cited

FOREIGN PATENT DOCUMENTS

| CN | 110182 A | 4/1995 |
|---|---|---|
| CN | 1965965 A | 5/2007 |
| CN | 103041080 A | 4/2013 |
| CN | 103768442 A | * 5/2014 |
| CN | 104173646 A | 12/2014 |
| CN | 111358902 A | 7/2020 |
| CN | 114558074 A | 5/2022 |

OTHER PUBLICATIONS

Southern Cross University "Could Natural Medicine Solve Recurrent Dizziness" Southern Cross University—National Centre for Naturopathic Medicine (NCNM), <URL: www.scu.edu.au/news/2024/dizziness-research/>, Jul. 18, 2024 (retrieved Jul. 9, 2025), 4 pages. (Year: 2024).*
Zhang L-Z et al, CN-103768442-A, machine translation, 12 pages. (Year: 2014).*
PCT/AU2024/050004 Published as WO 2024/148393, Jul. 18, 2024, CMOL Pharmaceuticals Australia Pty LTD.
Written opinion and search report for PCT/AU2024/050004, Jul. 18, 2024, CMOL Pharmaceuticals Australia Pty LTD.
Oh, H., et al. Chinese Herbal Medicine for Cervicogenic Dizziness: A Systematic Review and Meta-Analysis. Evid Based Complement Alternat Med. 2022:2425851 (2022) doi: 10.1155/2022/2425851.
Yuen Kut Lam, Hong Kong: "Kam Wo Tea". https://www.waiyeehong.com/drinks/teas-hot-drinks/herbal-teas/kam-WO-herbal-tea (downloaded May 7, 2025) Cumulative of Database accession No. 1617960, retrieved from: <https://www.gnpd.com/sinatra/recordpage/1617960/>.

* cited by examiner

*Primary Examiner* — Aaron J Kosar
(74) *Attorney, Agent, or Firm* — Brian S. Boyer; SYNDICATED LAW, PC

(57) ABSTRACT

A herbal medicine composition is provided for treating vertigo and/or dizziness comprising: *Alisma orientale* rhizome; *Atractylodes macrocephala* root; *Citri reticulatae pericarpium; Citri reticulatae viride pericarpium*; and Folium nelumbinis. The vertigo and/or dizziness of present interest should be understood to mean vertigo and/or dizziness arising as a result of water or dampness of the stomach. Methods of treating such vertigo and/or dizziness by administering the herbal medicine composition to a patient in need thereof are also provided.

17 Claims, 1 Drawing Sheet

HERBAL MEDICINE COMPOSITION AND METHODS OF USING SAME

CROSS-REFERENCE TO RELATED APPLICATIONS

This application is a "bypass" application under 35 U.S.C. 111 (a), a continuation of PCT/AU2024/050004, filed Jan. 8, 2024, which claims the benefit of Australian Application No. 2023900032, filed Jan. 9, 2023, each of which is hereby incorporated herein by reference in its entirety.

FIELD OF THE INVENTION

The present invention relates to a herbal medicine composition and methods of using same, and in particular to use of the composition for the treatment of vertigo and/or dizziness.

The invention has been developed primarily for use in the treatment of vertigo and/or dizziness and will be described hereinafter with reference to this application. It will, however, be appreciated that the invention is not limited to this particular field of use.

BACKGROUND OF THE INVENTION

There are several common causes of vertigo including, but not limited to, benign paroxysmal positional vertigo, head or neck injury, infection, medications, Meniere's disease, and migraine. Typically, persons suffering from vertigo will experience intense bouts of a sense of spinning or moving, which is both unpleasant and unsettling. On the other hand, persons suffering from dizziness typically experience feeling lightheaded, off-balance, and/or woozy. Known causes of dizziness include, but are not limited to, arrhythmia, cardiomyopathy, circulation problems, infections, motion sickness, and a sudden drop in blood pressure.

Known treatments for vertigo and dizziness include antibiotics, antihistamines, anti-nausea medications, beta-blockers, fluids, pain receptor blockers, pain relief medication, and rest. Such known treatments do not, however, alleviate vertigo and/or dizziness in many patients suffering from these conditions.

The present invention seeks to provide a herbal medicine composition and methods of using same, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE INVENTION

According to an aspect of the invention, there is provided a herbal medicine composition for treating vertigo and/or dizziness comprising: *Alisma orientale* rhizome; *Atractylodes macrocephala* root; *Citri reticulatae pericarpium*; *Citri reticulatae viride pericarpium*; and Folium nelumbinis. The vertigo and/or dizziness of present interest should be understood to mean vertigo and/or dizziness arising as a result of water or dampness of the stomach.

In an embodiment, the herbal medicine composition can comprise 50 to 60% *Alisma orientale* rhizome by dry weight.

In another embodiment, the herbal medicine composition can comprise 52 to 58% *Alisma orientale* rhizome by dry weight.

In another embodiment, the herbal medicine composition can comprise 56.82% *Alisma orientale* rhizome by dry weight.

In another embodiment, the herbal medicine composition can comprise 17 to 25% *Atractylodes macrocephala* root by dry weight.

In another embodiment, the herbal medicine composition can comprise 19 to 23% *Atractylodes macrocephala* root by dry weight.

In another embodiment, the herbal medicine composition can comprise 22.73% *Atractylodes macrocephala* root by dry weight.

In another embodiment, the herbal medicine composition can comprise 4 to 8% *Citri reticulatae pericarpium* by dry weight.

In another embodiment, the herbal medicine composition can comprise 6 to 7% *Citri reticulatae pericarpium* by dry weight.

In another embodiment, the herbal medicine composition can comprise 6.82% *Citri reticulatae pericarpium* by dry weight.

In another embodiment, the herbal medicine composition can comprise 4 to 8% *Citri reticulatae viride pericarpium* by dry weight.

In another embodiment, the herbal medicine composition can comprise 6 to 7% *Citri reticulatae viride pericarpium* by dry weight.

In another embodiment, the herbal medicine composition can comprise 6.82% *Citri reticulatae viride pericarpium* by dry weight.

In another embodiment, the herbal medicine composition can comprise 4 to 8% Folium nelumbinis by dry weight.

In another embodiment, the herbal medicine composition can comprise 6 to 7% Folium nelumbinis by dry weight.

In another embodiment, the herbal medicine composition can comprise 6.82% Folium nelumbinis by dry weight.

In another embodiment, the herbal medicine composition can comprise 56.82% *Alisma orientale* rhizome, 22.73% *Atractylodes macrocephala* root, 6.82% *Citri reticulatae pericarpium*, 6.82% *Citri reticulatae pericarpium*, and 6.82% Folium nelumbinis by dry weight.

According to another aspect there is provided a method of treating vertigo, the method comprising: providing a patient suffering from vertigo; administering to the patient one or more dose(s) of a herbal medicine composition, the herbal medicine composition comprising: *Alisma orientale* rhizome; *Atractylodes macrocephala* root; *Citri reticulatae pericarpium*; *Citri reticulatae viride pericarpium*; and Folium nelumbinis. The vertigo of present interest should be understood to mean vertigo arising as a result of water or dampness of the stomach.

In an embodiment, the herbal medicine composition can comprise 50 to 60% *Alisma orientale* rhizome, 17 to 25% *Atractylodes macrocephala* root, 4 to 8% *Citri reticulatae pericarpium* by dry weight, 4 to 8% *Citri reticulatae viride pericarpium*, and 4 to 8% Folium nelumbinis by dry weight.

In another embodiment, the herbal medicine composition can comprise 56.82% *Alisma orientale* rhizome, 22.73% *Atractylodes macrocephala* root, 6.82% *Citri reticulatae pericarpium*, 6.82% *Citri reticulatae pericarpium*, and 6.82% Folium nelumbinis by dry weight. In another embodiment, the one or more dose(s) can be administered about 4 hours apart.

According to another aspect of the invention, there is provided a method of treating dizziness, the method comprising: providing a patient suffering from dizziness; administering to the patient one or more dose(s) of a herbal medicine composition, the herbal medicine composition comprising: *Alisma orientale* rhizome; *Atractylodes macrocephala* root; *Citri reticulatae pericarpium; Citri reticulatae viride pericarpium*; and Folium nelumbinis. The dizziness of present interest should be understood to mean dizziness arising as a result of water or dampness of the stomach.

In an embodiment, the herbal medicine composition can comprise 50 to 60% *Alisma orientale* rhizome, 17 to 25% *Atractylodes macrocephala* root, 4 to 8% *Citri reticulatae pericarpium* by dry weight, 4 to 8% *Citri reticulatae viride pericarpium*, and 4 to 8% Folium nelumbinis by dry weight.

In an embodiment, the herbal medicine composition can comprise 56.82% *Alisma orientale* rhizome, 22.73% *Atractylodes macrocephala* root, 6.82% *Citri reticulatae pericarpium, 6.82% Citri reticulatae pericarpium*, and 6.82% Folium nelumbinis by dry weight.

In an embodiment, the one or more dose(s) can be administered about 4 hours apart.

This invention may also be said broadly to comprise in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

Other aspects of the invention are also disclosed.

BRIEF DESCRIPTION OF THE DRAWINGS

Notwithstanding any other forms which may fall within the scope of the present invention, a preferred embodiments of the invention will now be described, by way of example only, with reference to the accompanying drawings in which.

DESCRIPTION OF EMBODIMENTS

Figure 1:
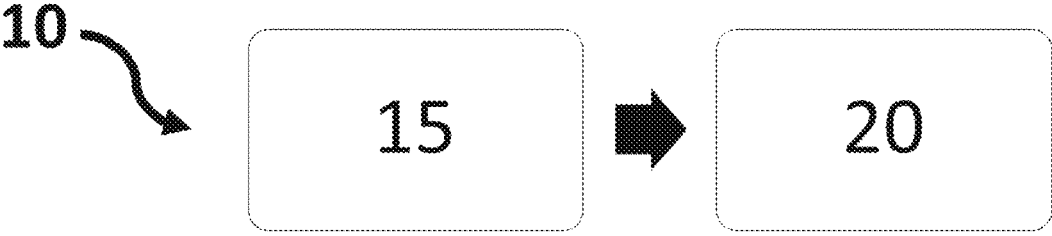
FIG. 1 shows a method of treating vertigo according to an aspect of the invention.

It should be noted in the following description that like or the same reference numerals in different embodiments denote the same or similar features.

Herbal Medicine

In an embodiment, a herbal medicine comprises *Alisma orientale* rhizome, *Atractylodes macrocephala* root, *Citri reticulatae pericarpium, Citri reticulatae viride pericarpium*; and Folium nelumbinis.

A person skilled in the art will appreciate that the term "*Alisma orientale* rhizome" as used herein should be understood to correspond to the common name "Ze xie"; the term "*Atractylodes macrocephala* root" as used herein should be understood to correspond to the common name "Bai zhu"; the term "*Citri reticulatae pericarpium*" as used herein should be understood to correspond to the common names "Chenpi" or "aged tangerine peel"; the term "*Citri reticulatae viride pericarpium*" as used herein should be understood to correspond to the common names "Qingpi" or "green tangerine peel"; the term "Folium nelumbinis" as used herein should be understood to correspond to the common names "He ye" or "lotus leaf".

In an embodiment, the herbal medicine composition comprises 50 to 60% *Alisma orientale* rhizome by dry weight.

In another embodiment, the herbal medicine composition comprises 52 to 58% *Alisma orientale* rhizome by dry weight.

In another embodiment, the herbal medicine composition comprises 56.82% *Alisma orientale* rhizome by dry weight.

In another embodiment, herbal medicine composition comprises 17 to 25% *Atractylodes macrocephala* root by dry weight.

In another embodiment, the herbal medicine composition comprises 19 to 23% *Atractylodes macrocephala* root by dry weight.

In another embodiment, the herbal medicine composition comprises 22.73% *Atractylodes macrocephala* root by dry weight.

In another embodiment, the herbal medicine composition comprises 4 to 8% *Citri reticulatae pericarpium* by dry weight.

In another embodiment, the herbal medicine composition comprises 6 to 7% *Citri reticulatae pericarpium* by dry weight.

In another embodiment, the herbal medicine composition comprises 6.82% *Citri reticulatae pericarpium* by dry weight.

In another embodiment, the herbal medicine composition comprises 4 to 8% *Citri reticulatae viride pericarpium* by dry weight.

In another embodiment, the herbal medicine composition comprises 6 to 7% *Citri reticulatae viride pericarpium* by dry weight.

In another embodiment, the herbal medicine composition comprises 6.82% *Citri reticulatae viride pericarpium* by dry weight.

In another embodiment, the herbal medicine composition comprises 4 to 8% Folium nelumbinis by dry weight.

In another embodiment, the herbal medicine composition comprises 6 to 7% Folium nelumbinis by dry weight.

In another embodiment, the herbal medicine composition comprises 6.82% Folium nelumbinis by dry weight.

In another embodiment, the herbal medicine composition comprises 56.82% *Alisma orientale* rhizome, 22.73% *Atractylodes macrocephala* root, 6.82% *Citri reticulatae pericarpium, 6.82% Citri reticulatae pericarpium*, and 6.82% Folium nelumbinis by dry weight.

Example 1: Herbal Medicine

A dose of the herbal medicine composition includes extracts of the following ingredients 14 grams *Alisma orientale* rhizome, 5.6 grams *Atractylodes macrocephala* root, 1.68 grams *Citri reticulatae pericarpium*, 1.68 grams *Citri reticulatae pericarpium*, and 1.68 grams Folium nelumbinis by dry weight. The ingredients are added to about 1 litre of water, the essence of the ingredients is extracted by heating the ingredients in the water to provide an ingredient extract concentrated down to about 300 millilitres. The ingredient extract is cooled to room temperature and consumed.

Example 2: Herbal Medicine

A dose of the herbal medicine composition includes extracts of the following ingredients 21 grams *Alisma ori-*

5

*entale* rhizome, 8.4 grams *Atractylodes macrocephala* root, 2.52 grams *Citri reticulatae pericarpium,* 2.52 grams *Citri reticulatae pericarpium*, and 2.52 grams Folium nelumbinis by dry weight. The ingredients are added to about 1 litre of water, the essence of the ingredients is extracted by heating the ingredients in the water to provide an ingredient extract concentrated down to about 300 millilitres. The ingredient extract is cooled to room temperature and consumed.

Example 3: Herbal Medicine

A dose of the herbal medicine composition includes extracts of the following ingredients 84 grams *Alisma orientale* rhizome, 33.6 grams *Atractylodes macrocephala* root, 10.08 grams *Citri reticulatae pericarpium,* 10.08 grams *Citri reticulatae pericarpium*, and 10.08 grams Folium nelumbinis by dry weight. The ingredients are added to about 1 litre of water, the essence of the ingredients is extracted by heating the ingredients in the water to provide an ingredient extract concentrated down to about 300 millilitres. The ingredient extract is cooled to room temperature and consumed.

The term "dose" as used herein should be understood to represent an amount dosed in dry mass for administration to a person in need of the herbal medicine. A person skilled in the art will appreciate that the herbal medicine may be consumed as deemed appropriate by the prescribing practitioner. Alternatively, the patient may elect to consume the herbal medicine in an ad hoc manner best suited to treating any relevant symptom experienced by the patient.

A dose of dry ingredients is typically provided as a powder in individual ready-to-prepare sachets. It will be appreciated that a dose of the herbal medicine composition can also be supplied as a capsule, emulsion, gel, granules, liquid, lozenge, paste, pill, tablet, tincture, and other dosages forms known to a person skilled in the art.

Methods of concentrating and/or drying the ingredient extract will be known to a person skilled in the art. Such methods may include boiling, convection drying, evaporation, freeze-drying/lyophilization, infrared radiation drying, microwave-vacuum drying, spray-drying, and the like.

Method of Treating Vertigo

In another embodiment (FIG. 1), a method of treating vertigo is general indicated by the reference number 10. The method of treating vertigo (10) includes providing a patient suffering from vertigo (15) and administering to the patient one or more dose(s) of a herbal medicine composition, the herbal medicine composition comprising: *Alisma orientale* rhizome, *Atractylodes macrocephala* root, *Citri reticulatae pericarpium, Citri reticulatae viride pericarpium*; and Folium nelumbinis (20).

The term "vertigo" as used herein should be understood to refer to a sensation, i.e., a symptom, experienced by a person suffering from vertigo where the person's environment, for example, a room, is spinning around the person.

In an embodiment, the herbal medicine composition comprises 50 to 60% *Alisma orientale* rhizome, 17 to 25% *Atractylodes macrocephala* root, 4 to 8% *Citri reticulatae pericarpium* by dry weight, 4 to 8% *Citri reticulatae viride pericarpium*, and 4 to 8% Folium nelumbinis by dry weight.

In an embodiment, the herbal medicine composition comprises 56.82% *Alisma orientale* rhizome, 22.73% *Atractylodes macrocephala* root, 6.82% *Citri reticulatae pericarpium,* 6.82% *Citri reticulatae pericarpium*, and 6.82% Folium nelumbinis by dry weight.

In an embodiment, the one or more dose(s) is/are administered about 4 hours apart.

6

Method of Treating Dizziness

Figure 2:
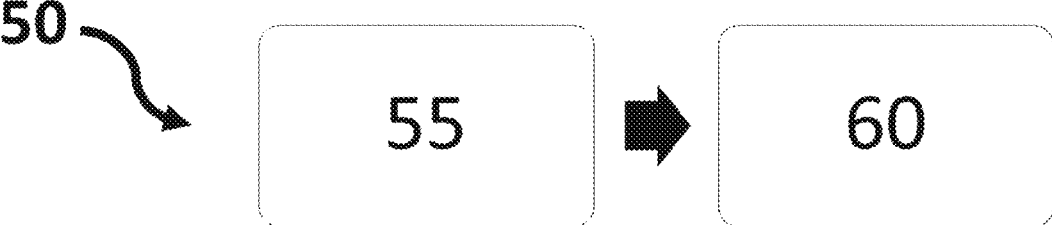
FIG. 2 shows a method of treating dizziness according to an aspect of the invention.

In another embodiment (FIG. 2), a method of treating dizziness is generally indicated by the reference numeral 50. The method (50) includes providing a patient suffering from dizziness (55) and administering to the patient one or more dose(s) of a herbal medicine composition, the herbal medicine composition comprising *Alisma orientale* rhizome, *Atractylodes macrocephala* root, *Citri reticulatae pericarpium, Citri reticulatae viride pericarpium*, and Folium nelumbinis (60).

The term "dizziness" as used herein should be understood to refer to a range of sensations, i.e., symptoms, experienced by a person suffering from dizziness experiences feeling disequilibrium, faint, light-headedness, presyncope, unsteady, weak, and/or woozy.

In an embodiment, the herbal medicine composition comprises 50 to 60% *Alisma orientale* rhizome, 17 to 25% *Atractylodes macrocephala* root, 4 to 8% *Citri reticulatae pericarpium* by dry weight, 4 to 8% *Citri reticulatae viride pericarpium*, and 4 to 8% Folium nelumbinis by dry weight.

In an embodiment, the herbal medicine composition comprises 56.82% *Alisma orientale* rhizome, 22.73% *Atractylodes macrocephala* root, 6.82% *Citri reticulatae pericarpium,* 6.82% *Citri reticulatae pericarpium*, and 6.82% Folium nelumbinis by dry weight.

In an embodiment, the one or more dose(s) is/are administered about 4 hours apart.

Example 1

A patient, who had awakened suffering severe vertigo both seated and standing had been prescribed medication for Meniere's disease but had not experienced relief from vertigo presented for treatment. The patient advised that her bowel movement was poor and fair sleeping patterns. A diagnosis of stomach qi deficiency, with water retention in the stomach was reached. The patient was prescribed the following dry ingredient equivalent dose: *Alisma orientale* rhizome—15 g, *Atractylodes macrocephala* root—5 g, *Citri reticulatae pericarpium*—2.5 g, and Rhizoma *Cyperi*—5 g to be taken twice a day for 3 days. At the time of consultation with the patient prior to taking the prescribed dry ingredient equivalent dose, the patient reported that she was experiencing vertigo that was extreme and unsettling.

During a follow up consultation, the patient reported that the vertigo was still severe and that she could not stand up. A diagnosis of stomach qi deficiency, with water retention in the stomach was considered still to be the case. The patient was prescribed the following dry ingredient equivalent dose: *Alisma orientale* rhizome—15 g, *Atractylodes macrocephala* root—5 g, *Citri reticulatae pericarpium*—2.5 g, and *Citri reticulatae viride pericarpium*—2.5 g to be taken 4 times a day for 3 days.

During a follow up consultation, the patient reported a 20% reduction the vertigo she was experiencing. A diagnosis of stomach qi deficiency, with water retention in the stomach was considered still to be the case. The patient was prescribed the following dry ingredient equivalent dose: *Alisma orientale* rhizome—15 g, *Atractylodes macrocephala* root—5 g, *Citri reticulatae pericarpium*—2.5 g, *Citri reticulatae viride pericarpium*—2.5 g, and Folium nelumbinis—2.5 g to be taken 4 times a day for 6 days. On follow up, the patient reported a complete reduction in the vertigo she was experiencing.

Example 2

A patient who suffered from dizziness upon waking up and standing up in the morning, dizziness when swinging her head, and occasional headaches that accompanied the dizziness presented for treatment. The patient's tongue colour was pink and had a thick white coating. The patient's heart beat was 82 beats per minute, which was slightly elevated and floating. The patient reported that her bowel movement, urine production, sleep patterns, and appetite were normal. A diagnosis of upright qi and stomach deficiency with water retention in the stomach was reached. The patient was prescribed the following dry ingredient equivalent dose: *Alisma orientale* rhizome—15 g, *Atractylodes macrocephala* root—5 g, *Citri reticulatae pericarpium*—2.5 g, *Citri reticulatae viride pericarpium*—2.5 g, and Folium nelumbinis—2.5 g to be taken once a day for 7 days. On follow up, the patient reported complete relief from dizziness after completing the course of above prescribed dry ingredient equivalent dose.

Example 3

A patient who suffered from dizziness on and off for 20 years presented for treatment. At the time of consultation, the patient reported that she experienced dizziness and coughing with mucus when lying down. The patient further reported that the dizziness was worse on wakening up in the morning. She also reported a blocked nose when lying down and consistently felt like her head was heavy and experienced motion sickness. The patient's tongue colour was pink and her tongue had a thick white coating. Her appetite was normal, but her sleep patterns were poor. The patient's heart beat was floating, weak, and slightly rapid, and her stomach pulse was sunken, wiry, and long. A diagnosis of stomach deficiency and holding of water producing mucus was reached. The patient was prescribed the following dry ingredient equivalent dose: *Alisma orientale* rhizome—20 g, *Atractylodes macrocephala* root—7.5 g, *Citri reticulatae pericarpium*—2.5 g, *Citri reticulatae viride pericarpium*—2.5 g, and Folium nelumbinis—2.5 g to be taken once a day for 7 days.

During a follow up consultation, the patient reported that her dizziness had improved about 20%, she was not producing discomforting mucus in her nose when lying down, and her sleep patterns had improved. She reported that she was still feeling heavy-headed. The patient's tongue colour was pink and her tongue had a thick white coating. Her bowel movement and urine production were normal, but her sleep pattern was poor. The patient's heart beat was floating, weak, and slightly rapid, and her stomach pulse was sunken, wiry, and long. A diagnosis of stomach deficiency and holding of water producing mucus was still to be the case. The patient was prescribed the following dry ingredient equivalent dose: *Alisma orientale* rhizome—20 g, *Atractylodes macrocephala* root—7.5 g, *Citri reticulatae pericarpium*—2.5 g, *Citri reticulatae viride pericarpium*—2.5 g, and Folium nelumbinis—2.5 g to be taken once a day for 7 days. On completion of the above prescribed course, the patient reported that she was experiencing no dizziness at all, no untoward mucus production, no feelings of a heavy head, and that she was sleeping much better.

Example 4

A patient experiencing intermittent dizziness and difficulty falling asleep presented for treatment. The patient complained that she felt heavy-headed and felt persistently tired. The patient's tongue was pink and head a white coating. The patient reported that her bowel movement, urine production, and appetite were normal, but sleep patterns were poor. A diagnosis of stomach holding water was reached. The patient was prescribed the following dry ingredient equivalent dose: *Alisma orientale* rhizome—20 g, *Atractylodes macrocephala* root—7.5 g, *Citri reticulatae pericarpium*—2.5 g, *Citri reticulatae viride pericarpium*—2.5 g, and Folium nelumbinis—2.5 g to be taken once a day for 14 days. On follow up, the patient reported that she had complete relief from dizziness.

Example 5

A patient experiencing vertigo daily typically before bedtime and occasional nausea presented for treatment. The patient's tongue colour was pink and the tongue had a white coating. A diagnosis of stomach holding water was reached. The patient was prescribed the following dry ingredient equivalent dose: *Alisma orientale* rhizome—20 g, *Atractylodes macrocephala* root—7.5 g, *Citri reticulatae pericarpium*—2.5 g, *Citri reticulatae viride pericarpium*—2.5 g, and Folium nelumbinis—2.5 g to be taken once a day for 7 days. On follow up, the patient reported complete relief from vertigo and nausea.

Example 6

A patient experiencing dizziness on and off for about 10 years, often feeling motion sickness and seasickness, feeling heavy-headed, and a blocked nose when lying down presented for treatment. The patient's tongue colour was pink and the tongue had a white coating. The patient reported that her bowel movement, urine production, and appetite were normal, but sleep patterns were poor. A diagnosis of stomach holding water was reached. The patient was prescribed the following dry ingredient equivalent dose: *Alisma orientale* rhizome —20 g, *Atractylodes macrocephala* root—7.5 g, *Citri reticulatae pericarpium*—2.5 g, *Citri reticulatae viride pericarpium*—2.5 g, and Folium nelumbinis—2.5 g to be taken once a day for 14 days. On follow up, the patient reported complete relief from dizziness.

Example 7

A patient experiencing a sensitive scalp since giving birth to her daughter 14 years previously presented for treatment. The patient had also been experiencing on and off dizziness for about 10 years. At the time of consultation, the patient reported slight dizziness, aching eyes, and that she felt tired. The patient's tongue colour was pink and the tongue had a white coating. The patient reported that her bowel movement, urine production, and appetite were normal, but sleep patterns were poor. The patient's heart beat was floating, weak, and slightly rapid, and her stomach pulse was sunken, wiry, and long. Her lung, kidney, and San Jiao pulses were also floating. A diagnosis of stomach holding water and hot stomach was reached. The patient was prescribed the following dry ingredient equivalent dose: *Alisma orientale* rhizome—20 g, *Atractylodes macrocephala* root—7.5 g, *Citri reticulatae pericarpium*—2.5 g, *Citri reticulatae viride pericarpium*—2.5 g, and Folium nelumbinis—2.5 g to be taken once a day for 7 days. On follow up, the patient reported complete relief from dizziness.

Example 8

A patient experiencing general heavy headedness, which was worse in the morning, presented for treatment. The patient reported that she was coughing with mucus production, experiences both motion and seasickness, which was sometimes accompanied by dizziness. The patient reported disturbed sleep with frequent awakening between 3-4 am. The patient's tongue colour was pink and the tongue had a white coating that was thick in the middle of the tongue. The patient reported that her bowel movement, urine production, and appetite were normal, but sleep patterns were poor. The patient's heart beat was floating, weak, and slightly rapid, and her stomach pulse was sunken, wiry, and long when in the deep position. A diagnosis of stomach holding water was reached. The patient was prescribed the following dry ingredient equivalent dose: *Alisma orientale* rhizome—15 g, *Atractylodes macrocephala* root—7.5 g, *Citri reticulatae pericarpium*—5 g, Pinelliae Teratae—5 g, and Folium nelumbinis—2.5 g to be taken once a day for 7 days.

During a follow up consultation, the patient reported that she was feeling about 20% better relative to heavy headedness, she was no longer coughing mucus, and was sleeping better, but was still feeling dizziness. The patient's tongue colour was pink and the tongue had a white coating. The patient reported that her bowel movement, urine production, and appetite were normal, but sleep patterns were poor. The patient's heart beat was floating, weak, and slightly rapid, and her stomach pulse was sunken, and wiry when in the deep position. A diagnosis of stomach deficiency and stomach holding water and dampness was reached. The patient was prescribed the following dry ingredient equivalent dose: *Alisma orientale* rhizome—20 g, *Atractylodes macrocephala* root—7.5 g, *Citri reticulatae pericarpium*—2.5 g, *Citri reticulatae viride pericarpium*—2.5 g, and Folium nelumbinis—2.5 g to be taken once a day for 7 days. On follow up, the patient reported that she was experiencing no dizziness, no feeling of heavy headedness, and sleeping much better.

Example 9

A patient reporting something stuck in his stomach presented for treatment. The patient reported that he was experiencing vertigo, feeling very tired, and that he frequently awakens at about 3-4 am. The patient reported that he often feels seasick and experiences motion sickness. The patient further reported that he experiences a blocked nose when sleeping or lying down. The patient further reported that he occasionally experienced coughing with mucus, and consistently feels heavy headed. The patient's tongue colour was pink and the tongue had a white coating. The patient reported that his bowel movement, urine production, and appetite were normal, but sleep patterns were poor. The patient's heart beat was floating, weak, and slightly rapid, and her stomach pulse was sunken, wiry, and long when in the deep position. A diagnosis of stomach deficiency and stomach holding water and dampness was reached. The patient was prescribed the following dry ingredient equivalent dose: *Alisma orientale* rhizome—20 g, *Atractylodes macrocephala* root—7.5 g, *Citri reticulatae pericarpium*—2.5 g, *Citri reticulatae viride pericarpium*—2.5 g, and Folium nelumbinis—2.5 g to be taken once a day for 7 days. On follow up, the patient report complete relief from the vertigo and feeling of having something stuck in his stomach.

Example 10

A patient experiencing intermittent dizziness, seasickness, and motion sickness presented for treatment. The patient reported that she had experienced bloating, frequent bowel movements, often more than 10 times a day, accompanied by significant mucus production after consuming wheat-based food products. She also reported experiencing coughing and mucus production. The patient reported that she has been diagnosed as gluten intolerant. The patient's tongue colour was pink and had a thin yellow coating. The patient reported that her bowel movement, urine production, and appetite were normal, but sleep patterns were poor. The patient's heart beat was floating, weak, and slightly rapid, and her stomach pulse was sunken, wiry, and long. A diagnosis of stomach deficiency and stomach holding water and mucus production was reached. The patient was prescribed the following dry ingredient equivalent dose: *Alisma orientale* rhizome—20 g, *Atractylodes macrocephala* root—7.5 g, *Citri reticulatae pericarpium*—2.5 g, *Citri reticulatae viride pericarpium*—2.5 g, and Folium nelumbinis—2.5 g to be taken once a day for 14 days. On follow up, the patient reported complete relief from frequent bowel movements, i.e., diarrhoea, after 7 days and complete relief from dizziness on completion of the above prescribed course.

For the purpose of this specification, where method steps are described in sequence, the sequence does not necessarily mean that the steps are to be carried out in chronological order in that sequence, unless there is no other logical manner of interpreting the sequence.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment but may. Furthermore, the particular features, structures or characteristics may be combined in any suitable manner, as would be apparent to one of ordinary skill in the art from this disclosure, in one or more embodiments.

Similarly, it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Description of Embodiments are hereby expressly incorporated into this Description of Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. It is understood, however, that embodiments of the invention may be practiced without these specific details. In other instances, well-known methods, structures, and techniques have not been shown in detail in order not to obscure an understanding of this description.

As used herein the term "and/or" means "and" or "or", or both.

As used herein "(s)" following a noun means the plural and/or singular forms of the noun.

In the claims which follow and in the preceding description of the invention, except where the context requires otherwise due to express language or necessary implication, the word "comprise" or variations such as "comprises" or "comprising" are used in an inclusive sense, i.e., to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

It is apparent from the above, that the arrangements described are applicable to the healthcare and wellness industries.

I claim:

1. A herbal medicine composition comprising:
Alisma orientale rhizome in an amount ranging from between 50 to 60% by dry weight of the composition:
Atractylodes macrocephala root in an amount ranging from between 17 to 25% by dry weight of the composition:
Citri reticulatae pericarpium in an amount ranging from between 4 to 8% by dry weight of the composition:
Citri reticulatae viride pericarpium in an amount ranging from between 4 to 8% by dry weight of the composition; and
Folium nelumbinis in an amount ranging from between 4 to 8% by dry weight of the composition.

2. The herbal medicine composition according to claim 1, wherein the herbal medicine composition comprises 52 to 58% Alisma orientale rhizome by dry weight.

3. The herbal medicine composition according to claim 1, wherein the herbal medicine composition comprises 56.82% Alisma orientale rhizome by dry weight.

4. The herbal medicine composition according to claim 1, wherein the herbal medicine composition comprises 22.73% Atractylodes macrocephala root by dry weight.

5. The herbal medicine composition according to claim 1, wherein the herbal medicine composition comprises 6.82% Citri reticulatae pericarpium by dry weight.

6. The herbal medicine composition according to claim 1, wherein the herbal medicine composition comprises 6.82% Citri reticulatae viride pericarpium by dry weight.

7. The herbal medicine composition according to claim 1, wherein the herbal medicine composition comprises 6.82% Folium nelumbinis by dry weight.

8. The herbal medicine composition according to claim 1, wherein the herbal medicine composition comprises 56.82% Alisma orientale rhizome, 22.73% Atractylodes macrocephala root, 6.82% Citri reticulatae pericarpium, 6.82% Citri reticulatae viride pericarpium, and 6.82% Folium nelumbinis by dry weight.

9. A method of treating vertigo, the method comprising:
providing a patient suffering from vertigo;
administering to the patient one or more doses of a herbal medicine composition, the herbal medicine composition comprising:
Alisma orientale rhizome in an amount ranging from between 50 to 60% by dry weight of the composition;
Atractylodes macrocephala root in an amount ranging from between 17 to 25% by dry weight of the composition;
Citri reticulatae pericarpium in an amount ranging from between 4 to 8% by dry weight of the composition;
Citri reticulatae viride pericarpium in an amount ranging from between 4 to 8% by dry weight of the composition; and
Folium nelumbinis in an amount ranging from between 4 to 8%, by dry weight of the composition.

10. The method of treating vertigo according to claim 9, wherein the herbal medicine composition comprises 56.82% Alisma orientale rhizome, 22.73% Atractylodes macrocephala root, 6.82% Citri reticulatae pericarpium, 6.82% Citri reticulatae viride pericarpium, and 6.82% Folium nelumbinis, by dry weight.

11. The method of treating vertigo according to claim 9, wherein multiple doses are administered, each of the multiple doses administered about 4 hours apart.

12. A method of treating a patient suffering from insomnia and/or motion sickness, the method comprising:
administering to the patient one or more dose(s) of a treatment composition comprising:
Alisma orientale rhizome in an amount ranging from between 50 to 60% by dry weight of the composition;
Atractylodes macrocephala root in an amount ranging from between 17 to 25% by dry weight of the composition;
Citri reticulatae pericarpium in an amount ranging from between 4 to 8% by dry weight of the composition;
Citri reticulatae viride pericarpium in an amount ranging from between 4 to 8% by dry weight of the composition; and
Folium nelumbinis in an amount ranging from between 4 to 8% by dry weight of the composition.

13. The method of claim 12, wherein the treatment composition comprises 56.82% Alisma orientale rhizome, 22.73% Atractylodes macrocephala root, 6.82% Citri reticulatae pericarpium, 6.82% Citri reticulatae viride pericarpium, and 6.82% Folium nelumbinis, by dry weight.

14. The method of claim 13, wherein multiple doses of the treatment composition are administered about 4 hours apart.

15. The method of claim 13, wherein the medicament is administered in a delivery dose of about 310 mg to 320 mg of the Alisma orientale rhizome, and subsequent doses spaced apart by four hours for a period of between one week to four weeks improves control of insomnia and/or motion sickness in a subject in need thereof.

16. A method for treating insomnia and/or motion sickness in a subject in need thereof, comprising administering the composition of claim 1, or acceptable salts thereof to the subject in multiple dosages spaced four hours apart.

17. The method of claim 16, wherein the composition has about 310 mg to 320 mg of the *Alisma orientale* rhizome, and the administering including subsequent doses spaced apart by four hours for a period of between one week to four weeks, which improves control of insomnia and/or motion sickness in a subject in need thereof.

\* \* \* \* \*